United States Patent [19]

Bauer

[11] Patent Number: 5,007,905
[45] Date of Patent: Apr. 16, 1991

[54] EYE DROP APPLICATOR

[76] Inventor: George C. Bauer, P.O. Box 825, Meredith, N.H. 03253

[21] Appl. No.: 481,634

[22] Filed: Feb. 20, 1990

[51] Int. Cl.$^5$ ............................................. A61M 35/00
[52] U.S. Cl. ..................................................... 604/295
[58] Field of Search ............... 604/295, 296, 297, 298, 604/299, 300, 301

[56] References Cited

U.S. PATENT DOCUMENTS 2,231,112  2/1941  Conner ................................ 604/295
2,837,128  6/1958  Marchant ........................... 604/295

FOREIGN PATENT DOCUMENTS 2142829  1/1985  United Kingdom ............... 604/295

Primary Examiner—John D. Yasko
Attorney, Agent, or Firm—Michael I. Kroll

[57] ABSTRACT

An improved eye drop applicator is provided for an eye dropper vial consisting of a cup having a lip portion to fit around an eyeball to keep the eye lid open. A sleeve has an internally threaded passageway extending from the apex of the cup. The internally threaded passageway is removably connected to an externally threaded neck of the eye dropper vial. The user can squeeze the eye dropper vial to direct an eye drop from a nozzle of the eye dropper vial onto the center of the eyeball.

1 Claim, 1 Drawing Sheet

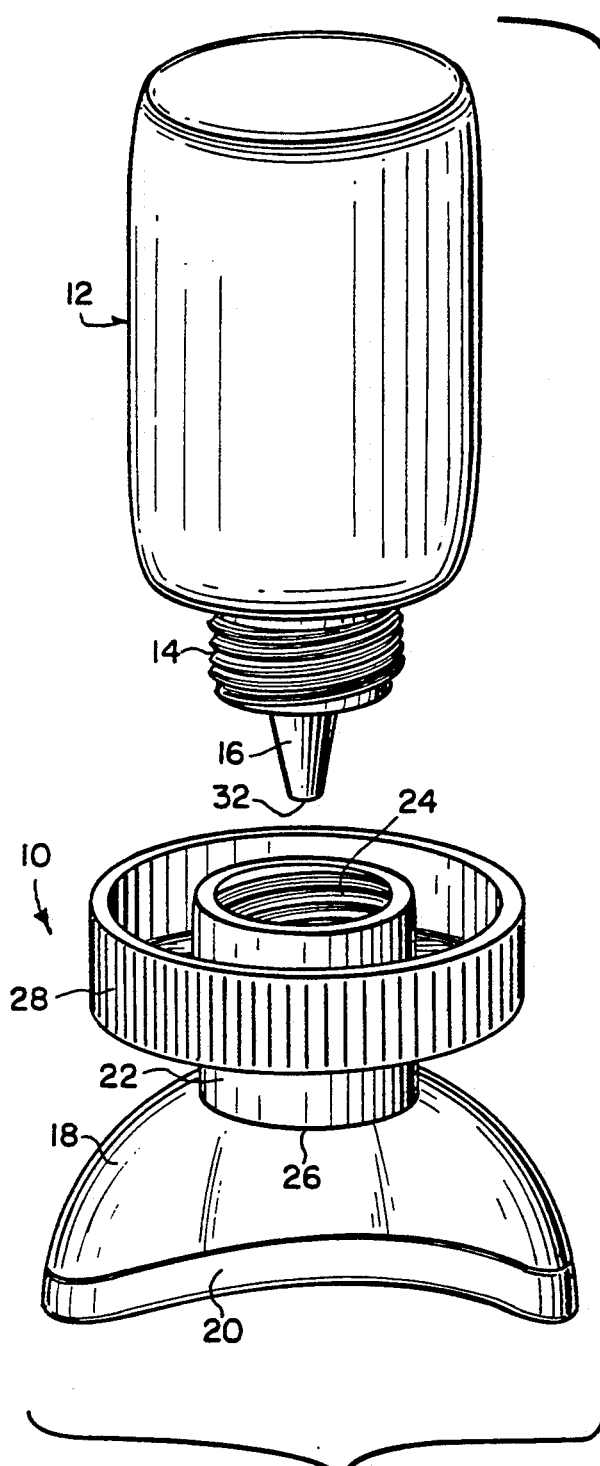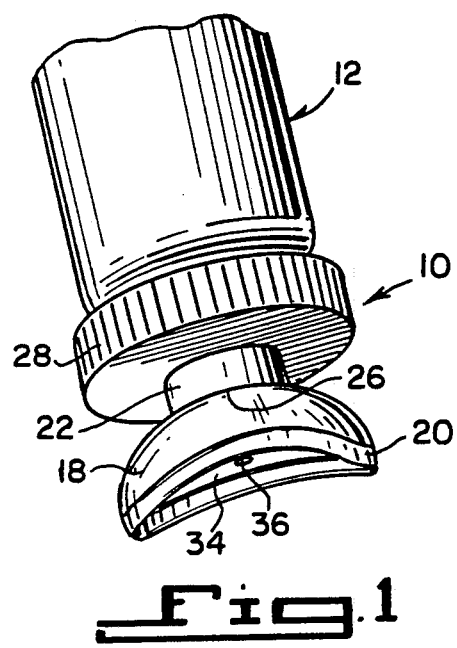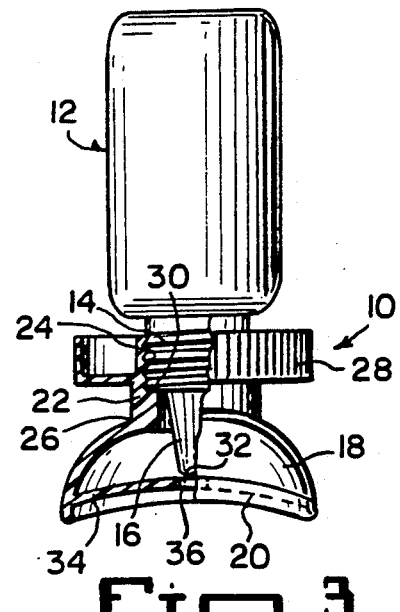

EYE DROP APPLICATOR

BACKGROUND OF THE INVENTION

1. Field of the Invention

The instant invention relates generally to eye cups and more specifically it relates to an improved eye drop applicator.

2. Description of the Prior Art

Numerous eye cups have been provided in prior art that are adapted to apply a liquid to the eyes to wash, clean or treat the eyes. For example, U.S. Pat. Nos. 1,244,498 to Heath; 1,692,143 to Strunz; 1,900,201 to Sager; 2,343,610 to Apfelbaum; 2,920,624 to Lerner et al; 4,111,200 to Sbarra et al and 4,834,727 to Cope all are illustrative of such prior art. While these units may be suitable for the particular purpose to which they address, they would not be as suitable for the purposes of the present invention as heretofore described.

SUMMARY OF THE INVENTION

A primary object of the present invention is to provide an improved eye drop applicator that will overcome the shortcomings of the prior art devices.

Another object is to provide an improved eye drop applicator that is removably connected to an eye dropper vial which will help hold the eye lid open while an eye drop is dispensed into the eyeball.

An additional object is to provide an improved eye drop applicator that is utilized as a holder for an eye dropper vial so as to direct an eye drop from the vial onto the center of the eye.

A further object is to provide an improved eye drop applicator that is simple and easy to use.

A still further object is to provide an improved eye drop applicator that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention attached to the threaded neck of an eye dropper vial.

FIG. 2 is an exploded perspective view of the invention removed from the threaded neck of the eye dropper vial.

FIG. 3 is an elevational view with parts broken away and in section showing the invention attached to the threaded neck of the eye dropper vial as in FIG. 1.

DETAILED DESCRIPTION OF THE PREFERRED EMBODIMENTS

Turning now descriptively to the drawings, in which similar reference characters denote similar elements throughout the several views, FIGS. 1 through 3 illustrate an improved eye drop applicator 10 for an eye dropper vial 12 of the type having an externally threaded neck 14 and a nozzle 16. The improved eye drop applicator 18 consists of a cup 18 having a lip portion 20 adapted to fit around an eyeball of a user (not shown) of the improved eye drop applicator 10 so as to keep the eye lid open. A sleeve 22 is provided having an internally threaded passageway 24 extending from the apex 26 of the cup 18. The internally threaded passageway 24 is removably connected to the externally threaded neck 14 of the eye dropper vial 12. The user can squeeze the eye dropper vial 12 to direct an eye drop from the nozzle 16 of the eye dropper vial onto the center of the eyeball.

An enlarged collar 28 is concentrically affixed onto the sleeve 22 to help aid the user of the improved eye drop applicator 10 to removably connect the internally threaded passageway 24 of the sleeve 22 to the externally threaded neck 14 of the eye dropper vial 12.

The internally threaded passageway 24 of the sleeve 22 has an annular shoulder 30 therein to prevent the tip 32 of the nozzle 16 of the eye dropper vial 12 from penetrating too far into the cup 18 thereby maintaining the nozzle 16 in a desired spaced relationship to the eyeball of the user of the improved eye drop applicator 10.

The improved eye drop applicator 10 further includes a protective shield 34 having a central aperture 36 and is affixed within the cup 18 with the central aperture 36 directly under the tip 32 of the nozzle 16 of the eye dropper vial 12. The protective shield 34 will help prevent the eyeball of the user of the improved eye drop applicator 10 from making contact with the tip 32 of the nozzle 16 of the eye dropper vial 12.

The cup 18, sleeve 22, enlarged collar 28 and protective shield 34 are made of plastic material and are integrally molded together to form the improved eye drop applicator 10.

To use the improved eye drop applicator 10 the user simply attaches the sleeve 22 to the neck 14 by rotating the enlarged collar 28. The lip portion 20 of the cup 18 is placed onto the eyeball to hold the eyelid open. The user the squeezes the eye dropper vial 12 to release an eye drop onto the center of the eyeball.

LIST OF REFERENCE NUMBERS 10 improved eye drop applicator
12 eye dropper vial
14 externally threaded neck of 12
16 nozzle of 12
18 cup of 10
20 lip portion on 18
22 sleeve of 10
24 internally threaded passageway in 22
26 apex of 18
28 enlarged collar on 22
30 annular shoulder in 24
32 tip of 16
34 protective shield in 18
36 central aperture in 34

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An improved eye drop applicator for an eye dropper vial of the type having an externally threaded neck and a nozzle, said improved eye drop applicator comprising:
    (a) a cup having a lip portion adapted to fit around an eyeball of a user of said improved eye drop applicator so as to keep the eye lid open;
    (b) a sleeve having an internally threaded passageway extending from the apex of said cup, in which said internally threaded passageway is removably connected to the externally threaded neck of the eye dropper vial, so that the user can squeeze the eye dropper vial to direct an eye drop from the nozzle of the eye dropper vial onto the center of the eyeball, said internally threaded passageway of said sleeve having an annular shoulder therein to prevent the tip of the nozzle of the eye dropper vial from penetrating too far into said cup thereby maintaining the nozzle in a desired spaced relationship to the eyeball of the user of said improved eye drop applicator;
    (c) an enlarged collar concentrically affixed onto said sleeve to help aid the user of said improved eye drop applicator to removably connect said internally threaded passageway of said sleeve to the externally threaded neck of the eye dropper vial; and
    (d) a protective shield having a central aperture and is affixed within said cup with said central aperture directly under the tip of the nozzle of the eye dropper vial, whereby said protective shield will help prevent the eyeball of the user of said improved eye drop applicator from making contact with the tip of the nozzle of the eye dropper vial.

* * * * *